United States Patent [19]

Bryne

[11] 4,269,390

[45] May 26, 1981

[54] CRYOSURGICAL INSTRUMENT

[75] Inventor: Michael D. Bryne, Vernon, Conn.

[73] Assignee: Brymill Corporation, Vernon, Conn.

[21] Appl. No.: 130,845

[22] Filed: Mar. 17, 1980

Related U.S. Application Data

[60] Continuation of Ser. No. 928,351, Aug. 14, 1978, abandoned, which is a division of Ser. No. 747,904, Dec. 6, 1976, Pat. No. 4,116,199.

[51] Int. Cl.³ ............... F16K 31/524; F16K 31/44
[52] U.S. Cl. ................................... 251/254; 251/246
[58] Field of Search ............ 251/254, 253, 263, 231, 251/246; 128/303.1; 74/55

[56] References Cited

U.S. PATENT DOCUMENTS

| 879,026 | 2/1908 | Beemer | 251/253 |
|---|---|---|---|
| 2,621,677 | 12/1952 | Curtis | 251/254 |
| 2,645,097 | 7/1953 | Posch | 128/400 |
| 4,116,199 | 9/1978 | Bryne | 128/303.1 |

FOREIGN PATENT DOCUMENTS

| 1011880 | 7/1952 | France | 251/246 |
|---|---|---|---|
| 441279 | 1/1936 | United Kingdom | 251/263 |

*Primary Examiner*—Alan Cohan
*Assistant Examiner*—A. Michael Chambers
*Attorney, Agent, or Firm*—M. P. Williams

[57] ABSTRACT

A cryosurgical instrument employing a standard, double-walled, metal vacuum bottle or dewer has a collar metallurgically bonded to the top of the dewer near the mouth thereof to provide machined threads for releasably engaging the delivery and control portion of the instrument to the reservoir portion of the instrument. The collar provides additional strength and support to the portion where the two walls of the dewer are joined to each other. A vent is provided in a bottom cap of the vacuum dewer. A valve directly in the cryogen delivery line is connected by a stem to a fulcrumed operating handle; a 360° fulcrum is used, to permit rotating the handle for thumb or finger operation with either the right or the left hand, as desired; rotation of the handle also rotates the valve stem so as to assist in freeing it from crystalline adhesion which may result from moisture in the cryogen or in the ambient air. In one embodiment, the 360° fulcrum has a cam surface which can be positioned wherever it is desired to cause the operating handle to be locked into the on position, regardless of its position of rotation. The fulcrum is adjustable for the relationship between the motion of the handle and the operation of the valve.

1 Claim, 2 Drawing Figures

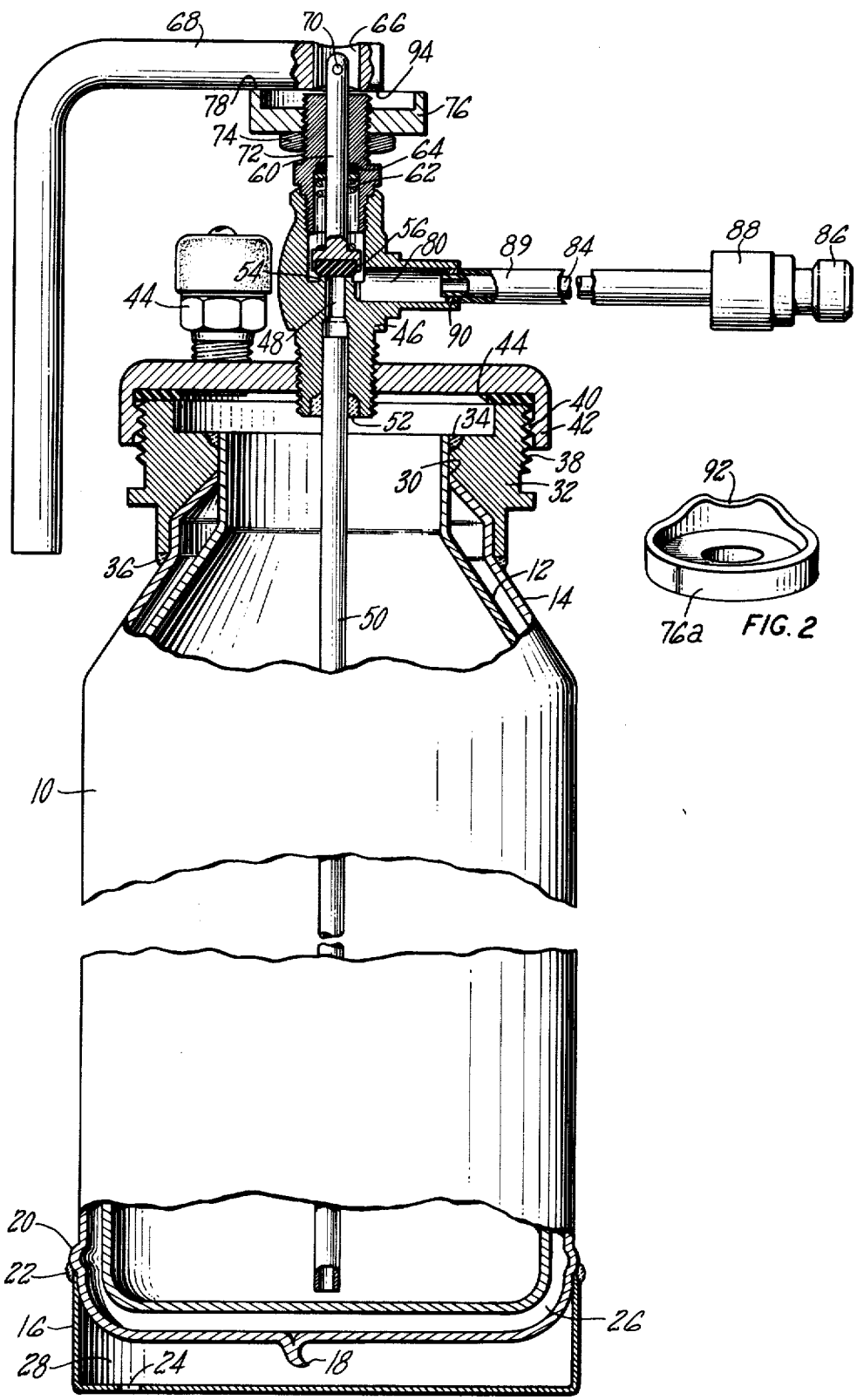

CRYOSURGICAL INSTRUMENT

CROSS REFERENCE TO RELATED APPLICATIONS

This application is a continuation of copending application Ser. No. 928,351, filed on Aug. 14, 1978, now abandoned, in turn a division of Ser. No. 747,904, filed on Dec. 6, 1976, now U.S. Pat. No. 4,116,199.

BACKGROUND OF THE INVENTION

1. Field of the Invention

This invention relates to cryosurgical instruments, and more particularly to directly valved, cryosurgical instruments.

2. Description of the Prior Art

The first hand held cryosurgical instrument for general surgical use is set forth in my U.S. Pat. No. 3,534,739. That instrument controlled the venting of continuously, self-boiling cryogen in order to force the delivery of liquid cryogen as desired. Since the device is continuously vented, except against the pressure induced by the operator in manipulating the vent closing valve thereof, no pressure relief was necessary, and none of the liquid cryogen flowed through the valve. As clinical history developed in the years following the introduction of this hand held cryosurgical unit, more and more usage was found therefore.

In attempts to provide lower cost cryosurgical units which would utilize the liquid cryogen more economically by reducing the rate of boiling thereof while in the reservoir of a cyrosurgical instrument, standard, commercial vacuum bottles having dual metallic walls have been used as the basis for construction of cryosurgical instruments. These devices, it has been found, have numerous drawbacks. First of all, since the intent is to conserve nitrogen, the devices were not provided with normally open vents, the closing of which would force liquid through the delivery tube, but rather were provided with valves directly in the cryogen delivery tube, with pressure relief valves to avoid the buildup of excess pressure therein.

The provision of low cost valves capable of being used directly in the liquid cryogen delivery line has given rise to additional problems, such as freezing of the valve in either the open position or in the closed position, or both. No provision has heretofore been made to alleviate the freezing when it occurs, other than setting the instrument aside until it can thaw suitably from ambient temperature.

The cryosurgical instrument disclosed in my aforementioned patent utilizes a control valve which is symmetrically disposed with respect to the delivery tube, and is therefore equally useful for right-handed and left-handed surgeons. However, it is limited to operation by the thumb (or in some equivalent manner). Certain of the instruments which have been offered as low cost instruments are designed in a fashion which totally commits them to preferential use either by the right hand or the left hand. Thus, not only is a right-handed instrument likely to be unwieldly for a left-handed surgeon to use, interchange between the two hands of a surgeon as desired or between surgeons of different handedness is hampered by designs which are available in the art.

SUMMARY OF THE INVENTION

Objects of the present invention include improvements in hand held, directly valved cryosurgical instruments According to the invention, a valve directly in the cryogen feed line consists of a stem with a valve seat pad theron, the stem extending externally to an operating handle, the handle rests against a fulcrum such that it is operable to slide the valve stem longitudinally the fulcrum is adjustable upwardly and downwardly so as to permit altering the relationship between handle motion and resultant valve motion to suit the desires of the operator. The adjustable fulcrum means of the invention can use a threaded lock nut cooperating with an unthreaded fulcrum, or both a threaded fulcrum and a lock nut. The invention permits adjustment for surgically acceptable handle motion relationship to cryogen flow. This permits the cryosurgical instruments to be mass produced from simple, available parts and subsequently adjusted for proper operation.

The present invention permits manufacture of a highly reliable and safe, as well as versatile, cryosurgicalinstrument utilizing mainly standard components which are widely available in the art.

The foregoing and other objects, features and advantages of the present invention should become more apparent in the light of the following detailed description of a preferred embodiment thereof, as illustrated in the accompanying drawing.

BRIEF DESCRIPTION OF THE DRAWING

FIG. 1 is a partially sectioned side elevation view of a preferred embodiment of the invention; and FIG. 2 is a perspective view of an alternative embodiment of a fulcrum which may be used in the embodiment of FIG. 1.

DESCRIPTION OF THE PREFERRED EMBODIMENTS

Referring now to FIG. 1, the reservoir of a cryosurgical instrument, useful with the present invention comprises a standard commercial vacuum bottle 10 which consists mainly of an inner wall 12, an outer wall 14 and a bottom pan 16. The bottom pan protects a vacuum seal such as a pinch tube 18 which is used to evacuate the bottle and then sealed off in a fashion known to the art. To support the pan 16, the outer wall may have an annular crease 20 formed therein, and the pan may be suitably bonded to the outer wall such as by brazing or welding 22. A hole 24 is provided in the pan 16 so that in the event that the inner wall 12 is ruptured, allowing cryogen to flow into the normally-evacuated void 26 between the two walls 12, 14, the danger of the vacuum seal opening and allowing gaseous pressure to build up in the void 28 within the pan 16 is eliminated. Therefore, this design overcomes the danger of a pressure buildup which could cause the pan 16 to be violently expelled from the reservoir and cause injury.

At the top of the vacuum bottle 10, the walls 12, 14 are normally joined by brazing or welding 30. Typically, the final, upper portion of the outer wall 14 may have rolled or stamped threads therein to receive a drinking cup, in a fashion well known in the art (although these are not shown herein for simplicity). The joint 30 is protected against rupture by the buildup of pressure between the walls 12, 14 which might result if there is a breach in the inner wall while the vacuum bottle is containing cryogen, by means of a heavy metal collar 32 which is metallurgically bonded as at 34 and 36 so as to form a strong unitary structure. The collar 32 is also provided with machined threads 38 in order to facilitate releasable joinder with similar threads 40 of a cap 42 which forms the basic foundation structure of the control and delivery portion of the instrument. The cap 42 is sealed to the collar 32 by a silicone gasket 44. The machined threads 38, 40 permit removal of the cap 42 for filling of the unit, while at the same time preventing the cap 42 from inadvertently being sprung from the collar 32 as from dropping or from excessive pressure. The cap 42 is drilled and tapped so as to receive a standard pressure relief valve 44 that limits the buildup of pressure within the instrument to a desired amount, which may be on the order of 10 or 15 psi. The cap is also drilled and tapped so as to receive a valve structure 46 which includes a central bore 48 that receives a hollow tube 50 which is brazed or otherwise bonded (as at 52) to the valve member 46. The valve has an annular seat 54 which cooperates with a silicone valve pad 56 mounted in a valve stem 60. The valve stem 60 is normally forced downwardly as seen in FIG. 1 so as to cause closure of the valve by means of a spring 62. The valve stem 60 is sealed by a silicone 0-ring 64. The top of the valve stem fits within an oval or elongated hole 66 within a handle 68 and is rotatably fixed thereto by means of a pin 70. The handle 68 may simply comprise a bent metal rod. The top of the valve member 46 is provided with threads 72 which receive an adjusting nut 74 that controls the amount of play (vertically as seen in FIG. 1) of a dish like structure which provides an annular fulcrum 76. When the handle 68 is rocked counterclockwise (as seen in FIG. 1) about the pin 70, its surface 78 will contact the upper surface of the fulcrum 76 causing the pin 70 and therefore the valve stem 60 to be raised, thereby opening the valve. Since the valve stem 60 is fully rotatable within the valve member 46, and since the fulcrum 76 is annular in shape, the handle 68 and valve stem 60 may be rotated in any desired position about the axis of the valve stem 60 and still be fully operable. Rotation of the handle 68 about the axis of the valve stem 60 will also cause rotation of the valve pad 56 and tend to free it when it may have adhered by ice to the valve seat 54. Similarly, should moisture cause freezing of the valve stem 60 to the O-ring 64, rotation of the handle about the valve stem axis will shear the ice and free the device from being struck in an open position. When the valve stem 60 is in the upward position as a result of movement of the handle 68, the cryogen can flow up the tube 50 through the central bore 48 and into a lateral bore 80. Into the bore 80 there is fitted a tube 84 which is of somewhat smaller diameter than the bore 80. The reason for this is to facilitate a certain amount of vaporization of the liquefied gas cryogen prior to its reaching an orifice 86 which may be joined to the tube 84 by a standard fitting 88 in the fashion described in my aforementioned patent. This gasification results from the fact that the cap 42, the valve member 46, even the pressure relief valve 44, the fulcrum 76 and the handle 68 may all be heat conducting metal, thereby accepting heat from the ambient which can be given off to the cryogen within the bore 80 thereby tending to gasify it; by having the tube 84 of a somewhat smaller diameter, the amount of liquid which may reside in the tube 84 during operation is limited, thereby limiting the cooling rate just prior to delivery to a rate which is substantially low with respect to the natural flow of heat into the instrument to permit a certain amount of gasification of the cryogen to result. As an example, the structure shown in FIG. 1 may provide at its orifice 86 cryogen of roughly an equal mixture of gas and liquid, perhaps predominantly gas. In order to facilitate joinder of the smaller tube 84 within the larger bore 80, a metal washer filler 90 may be bonded both to the valve member 46 and to the tube 84 metallurgically, such as by brazing.

Referring now to FIG. 2, an additional aspect of the present invention includes a fulcrum 76a of a generally annular shape, but having a cam portion 92 thereon such that rotation of the cam portion 92 to a point at the surface 78 of the handle 68 will cause a surface of the handle 94 to contact the upper shoulder of the threads 72 and thereby cause the valve stem 60 to be lifted, whereby the instrument is operable in a steady state on condition.

As described, the cryosurgical instrument in accordance with the present invention is substantially all durable metal, having only a silicone valve pad and a silicone seal therein. The inline valve is substantially freeze proof, and is additionally freeable by rotation about the longitudinal axis of the valve stem by means of the handle. The annular fulcrum allows motion of the handle in substantially any position within 360°, and also permits a lock-on type of operation with the embodiment of FIG. 2, without regard to the rotary position of the handle.

The tube 84 may be sheathed by a non-sticking plastic tubing 89, or the like, if desired. The elongated hole 66 allows free motion of the valve stem 60 therewithin without regard to the position of the adjusting nut 74. The valve structure may be modified from any of several which are of standard design in the market, such as a Hoke 1511 M 4 B.

Although the invention has been shown and described with respect to preferred embodiments thereof, it should be understood by those skilled in the art that various changes, omissions and additions in the form and detail thereof may be made thereto and therein without departing from the spirit and scope of the invention.

Having thus described typical embodiments of my invention, that which I claim as new and desire to secure by Letters Patent of the United States is:

1. An improved cyrosurgical instrument including:
   application means for cryosurgical extraction of heat from living tissue in the treatment thereof;
   reservoir means for holding liquefied gas cryogen;
   and operator-controlled means for conveying a cryogen from said reservoir means to said application means; in which the improvement is in said operator-controlled means and comprises:
   a valve member having a central bore and an annular valve seat disposed along said bore, an upstream end of said bore on one side of said valve seat being in fluid communication with said reservoir, and a downstream end of said bore on the other side of said valve seat being in fluid communication with application means;
   a valve stem having an axis, said valve stem being rotatably and slidably disposed within said bore;
   a valve pad disposed on said valve stem, said valve stem being longitudinally slidable along said axis so as to render said valve member closable with said valve pad seated against said valve seat or openable with said valve pad disposed apart from said valve seat;

a pivot disposed at an end of said valve stem remote of said valve pad, said pivot being perpendicular to said axis of said valve stem;

a handle member rotatably disposed by said pivot;

an annular fulcrum means disposed coaxially on said valve member remotely of said valve seat and adjacent to said handle member in a position related to the position of said pivot so that angular rotation of said handle member about said pivot and said annular fulcrum means causes said valve stem to slide longitudinally away from said valve seat, regardless of the rotary orientation of said valve stem said annular fulcrum means having internal threads; and wherein said valve member has external threads coaxially disposed with respect to said bore and coacting with the threads of said annular fulcrum means, whereby the position of said annular fulcrum means is adjustable relative to the position of said pivot along said external threads.

* * * * *